Figure 1:
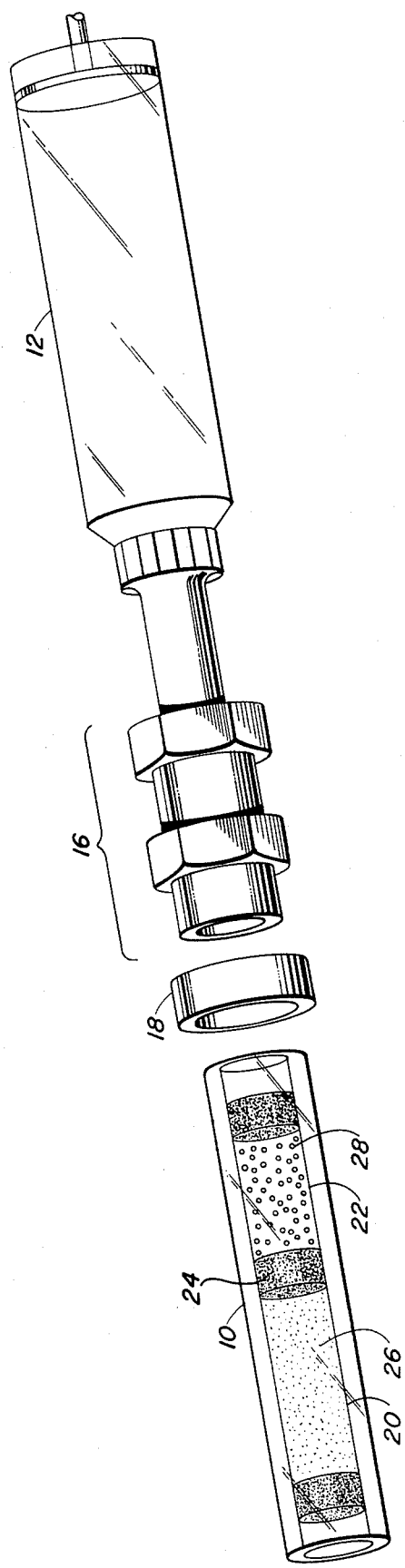

United States Patent [19]

Heller et al.

[11] Patent Number: 4,496,520

[45] Date of Patent: Jan. 29, 1985

[54] FIELD DETECTION OF 2,4,6-TRINITROTOLUENE IN WATER BY ION-EXCHANGE RESINS

[75] Inventors: Carl A. Heller; Eric D. Erickson, both of China Lake, Calif.; Sterling R. Greni, Newport, R.I.

[73] Assignee: The United States of America as represented by the Secretary of the Navy, Washington, D.C.

[21] Appl. No.: 380,321

[22] Filed: May 20, 1982

[51] Int. Cl.³ .................. G01N 33/18; G01N 33/22
[52] U.S. Cl. .................................. 422/60; 436/110
[58] Field of Search .............. 422/55, 58, 56, 59, 422/60, 61, 102, 69, 70; 436/110

[56] References Cited

U.S. PATENT DOCUMENTS 3,378,348 4/1968 McConnaughey .............. 422/60
4,073,726 2/1978 Okamoto et al. .............. 210/45
4,108,604 8/1978 Heller .............................. 23/230 R
4,125,376 11/1978 Razulis .......................... 23/230 R
4,150,089 4/1979 Linet .............................. 422/102
4,254,082 3/1981 Schick et al. ................... 422/61

Primary Examiner—Arnold Turk
Attorney, Agent, or Firm—Robert F. Beers; W. Thom Skeer; Bruce H. Cottrell

[57] ABSTRACT

A method and a device for the detection of trinitrotoluene (TNT) in effluent water from the purification apparatus of ammunition plants is described. The tube detector utilizes a basic oxide section to convert the TNT to its Meisenheimer anions, followed by an alkyl quaternary ammonium chloride ion-exchange resin which collects the colored anions. The length of the resultant stain is proportional to the concentration of TNT in the water.

13 Claims, 1 Drawing Figure

FIELD DETECTION OF 2,4,6-TRINITROTOLUENE IN WATER BY ION-EXCHANGE RESINS

BACKGROUND OF THE INVENTION

This invention relates to a method of rapid on-site determination of concentration of 2,4,6-trinitrotoluene (TNT) in effluent water.

The effluent water from the purification apparatus of ammunition plants may often contain traces of TNT. 2,4,6-Trinitrotoluene ($\alpha$-TNT) is a blood and liver toxin, which can be absorbed through the skin, lungs, or gastrointestinal tract. In addition, photochemical degradation of dilute aqueous solutions of $\alpha$-TNT result in a phenomenon aptly called "pink water." In order to reduce these undesirable effects and to meet regulatory standards, ammunition plants filter their effluent water though columns of strong absorbers such as activated carbon or diatomaceous earth. These columns will not extract unlimited quantities of contaminants. It is therefore desirable to determine when breakthrough occurs in order that the column be replaced.

At the present time, breakthrough is determined by collecting a sample of the effluent from the columns and analyzing it in a laboratory. Techniques of analysis presently employed include: oxidation followed by colorimetric determination of the nitrate content; extraction into an organic phase followed by analysis by gas chromatography; or reverse-phase high-pressure liquid chromatography. Detection has also been reported by measuring the fluorescence quenching of $\alpha$-TNT trapped on a fluorescent ion-exchange resin. All of these analytical methods are time consuming and require chemical training to perform. It would be beneficial to be able to utilize a field detector which would be portable, provide a rapid analysis, utilize small sample volumes, be free of interferences, yield easily obtained results, require little technical training to use, a present no health hazards to inexperienced technicians.

SUMMARY OF THE INVENTION

The objects of this invention are achieved by providing a method and a device for the determination of concentration of trinitrotoluene in fresh water. A sample of TNT bearing water is introduced into a 2 section tube, containing a reagent in one section and an ion exchange resin in the other. The reaction caused, stains the ion exchange resin and the length of the stain is proportional to the concentration of TNT in water. The length of stain is compared with a previously set standard and the concentration of TNT is determined.

PREFERRED EMBODIMENT OF THE INVENTION

The advantages of the method and device will become apparent upon consideration of the following disclosure of the invention; especially when taken in conjunction with the accompanying drawing wherein FIG. 1 illustrates an embodiment of this invention.

The invention is demonstrated by the following example performed in the laboratory. The apparatus as shown in FIG. 1 includes a transparent indicator tube (10), and syringe (12) connected by a fitting (16). The fitting (16) is attached to the indicator tube (10) with the aid of Teflon ferrule (18).

The syringes used are 10 cc, 21 g, 1½ Luer-Lok tip syringes manufactured by Becton, Dickinson and Company (Catalog number 5643). The invention is not limited to these specific syringes or connectors and any comparable equipment could be used.

The indicator tube (10) is made out of glass and its dimensions are ID=0.4 mm, and OD=0.6 mm. The tube is divided into two compartments: the resin compartment (20) and reagent compartment (22). The compartments are separated from each other and formed by a pack of glass wool (24) about 3 mm thick. The resin compartment (20) is filled with a strongly basic anion exchange resin (26) and is about 40 mm long and takes about 0.3 g of the resin. The reagent compartment (22) contains glass beads (28) impregnated with a base. Glass beads, used in the reagent section to improve flow characteristics, were type SL (0.7–1.2 mm) manufactured by PCR, Incorporated.

The glass beads are mixed with CaO in the ratio 99.4 to 0.6 by weight respectively. Enough water is added to form a paste which is dried in a vacuum oven. The reagent compartment (22) is filled with 0.3 g of impregnated beads and takes a space of about 23 mm in the indicator tube.

Military grade $\alpha$-TNT (m.p 80.2° C.), recrystallized in benzene and stored in the dark was used as a standard.

A 10 cc aliquot of the solution of interest is drawn up into the plastic syringe (12). The concentration of a 10 ppm TNT standard did not change measurably after being left in the plastic syringes for 4 days. After fastening the indicator tube (10) and fitting it to the syringe (12), the solution of interest is pushed through the tube at a constant rate, typically at 1.5 cc/minute.

The basic oxide section of the indicator tube converts the $\alpha$-TNT to its highly colored Meisenheimer anion. This anion strongly attaches to the cations of the anion exchange resin forming a reddish discoloration of the resin, the length of which is proportional to the concentration of TNT in the solution of interest. The concentration of TNT is determined by comparing the stain length with the standards previously made for various concentrations. The proposed chemical reactions in the indicator tube are:

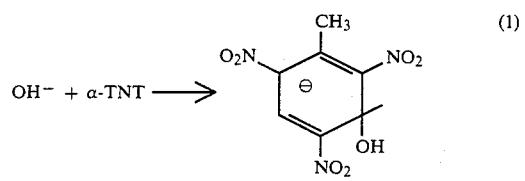

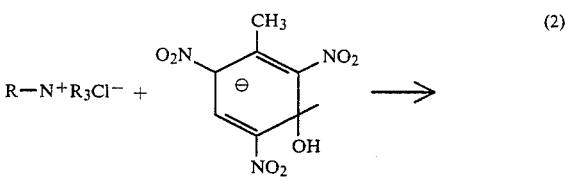

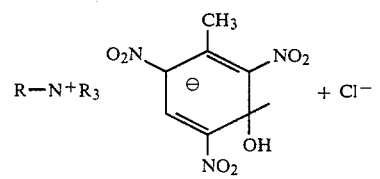

Using the described method one can detect concentrations as low as 0.1 ppm TNT. Further by using smaller bore tubing or larger sample volumes TNT concentrations lower than 0.1 ppm can be detected.

Anion exchange resins from several manufacturers were used and found suitable. Strongly basic anion exchange resins that were lightly-colored yielded the best results and permitted visual observation of the collected anion. Most of the work was done using the chloride form of Dowex 1×10 (Reg. TM of Dow Chemical Co.). This is a strongly basic polystyrene resin whose active groups are of the form $PhCH_2N^+(CH_3)_3Cl^-$. The 50–100 mesh size range was utilized for most of this work. Also, the colored TNT anion must be strongly absorbed by the resin. The best results were obtained with an alkyl quaternary amine chlorine exchange resin. Any base which is strong enough to react with $\alpha$-TNT to form the colored anion would be useful. Among the strong bases which have been successfully used include BaO, CaO, $Mg(OH)_2$, and MgO.

Increasing the sample volume increases the time necessary to perform the analysis. Sample volumes of 5–50 cc have been used successfully. At a flow rate of 1.5 cc/min, a 5 cc sample volume yields results in 3.3 minutes. However, the stain length produced is so small as to make it difficult to discern small differences in concentration. This problem is alleviated by using a 50 cc sample volume. However, this sample volume takes 33 minutes to obtain results and defeats the goal of rapid analysis time. A compromise sample volume of 10 cc is routinely used. This volume provides results in 6.7 minutes and improves the ability to discern small differences in concentration. Increasing the sample volume produces a corresponding increase in the stain length. A 50 cc sample of a 0.1 ppm $\alpha$-TNT solution produces approximately the same stain length as 10 cc of a 0.5 ppm solution.

No discoloration of the resin was observed from tap water, RDX, NaOH, $C_2H_5OH$, $CH_3COCH_3$, $C_6H_5CH_3$, $NaNO_2$, $NaNO_3$, NaCl, CaO, $Ca(OH)_2$, MgO, $Al_2O_3$, $NH_4Cl$, or $NH_4NO_3$.

In order to determine the effect of "pink water" on the stain length, 10.0 ppm $\alpha$-TNT solutions were exposed to sunlight over a weekend. Reverse phase liquid chromatography showed that up to 80% of the TNT had photolytically decomposed. These solutions were diluted to a final concentration of 1.0 ppm TNT. The stain lengths obtained from these solutions were identical to that obtained from a 1.0 ppm $\alpha$-TNT standard.

Solutions of 1.0 ppm $\alpha$-TNT at temperatures between 2.3° and 46° C. were passed through the indicator tubes. No. differences were detected among stain lengths at various temperatures.

TNT Detection. As finally adopted, this method passes a 10 ccm sample volume through an indicator tube at 1.5 cc/min. The idicator tube's presection consists of 0.3 g of 0.6% CaO-coated glass beads. The indicator section consists of 0.3 g of the chloride form of Dowex 1×10 anion exchange resin.

Different concentrations of $\alpha$-TNT produce different stain lengths. An estimate of the TNT concentration is obtained by comparing the stain length of the unknown to that of a standard. The smallest $\alpha$-TNT concentration which can be reproducibly detected and distinguished from a blank is 0.1 ppm. This could be improved by using smaller bore tubing or a larger sample volume. Using a 10 cc sample volume, a difference of at least 0.3 ppm is needed to differentiate between two concentrations.

While the invention has been described in terms of preferred embodiments thereof, it is not to be so limited since changes and alterations may be made therein which are within the full and intended scope of the appended claims.

We claim:

1. An indicator tube for the detection of the presence of trinitrotoluene in fresh water comprising:
    a transparent tube having a first compartment and a second compartment, and having an entry end and an exit end allowing a flow through passage;
    glass wool separating said first and second compartments, within said transparent tube;
    strong base impregnated glass beads containing said strong base in an amount effective to convert trinitrotoluene to a highly colored anion, and retained within said first compartment, said first compartment positioned adjacent to said entry end; and
    a strongly basic anion exchange resin having an affinity for said highly colored anion, and retained within said second compartment, said second compartment positioned adjacent to said exit end for enabling observation of the length of color change caused by said highly colored anion combining with said exchange resin in said second compartment, for comparison with a set standard.

2. An indicator tube according to claim 1 wherein said strong base is selected from the group consisting of CaO, MgO, BaO and $Mg(OH)_2$.

3. An indicator tube according to claim 1 wherein said strong base is BaO.

4. An indicator tube according to claim 1 wherein said strong base is CaO.

5. An indicator tube according to claim 1 wherein said strong base is MgO.

6. An indicator tube according to claim 1 wherein said strong base is $Mg(OH)_2$.

7. An indicator tube according to claim 1 wherein said strong base impregnated glass beads comprise about 99.4 percent by weight glass beads and 0.6 percent by weight strong base.

8. An indicator tube according to claim 1 wherein said strongly basic anion exchange resin is an alkyl quaternary amine chloride exchange resin.

9. An indicator tube according to claim 8 wherein said strong base is selected from the group consisting of CaO, MgO, BaO and $Mg(OH)_2$.

10. An indicator tube according to claim 8 wherein said strong base is BaO.

11. An indicator tube according to claim 8 wherein said strong base is CaO.

12. An indicator tube according to claim 8 wherein said strong base is MgO.

13. An indicator tube according to claim 8 wherein said strong base is $Mg(OH)_2$.

* * * * *